United States Patent [19]

Gaffney

[11] Patent Number: 4,849,571
[45] Date of Patent: Jul. 18, 1989

[54] HYDROCARBON PRODUCTION
[75] Inventor: Anne M. Gaffney, West Chester, Pa.
[73] Assignee: Atlantic Richfield Company, Los Angeles, Calif.
[21] Appl. No.: 196,702
[22] Filed: May 20, 1988
[51] Int. Cl.$^4$ ................................ C07C 2/04
[52] U.S. Cl. .................. 585/500; 585/502; 585/659; 585/661
[58] Field of Search ............... 585/659, 661, 512

[56] References Cited
U.S. PATENT DOCUMENTS

| | | | |
|---|---|---|---|
| 3,325,465 | 6/1967 | Jones | 585/516 |
| 4,450,310 | 5/1984 | Fox | 585/500 X |
| 4,523,050 | 6/1985 | Jones | 585/500 |
| 4,659,743 | 4/1987 | Rao | 502/66 X |

Primary Examiner—William R. Dixon, Jr.
Assistant Examiner—James M. Hunter, Jr.
Attorney, Agent, or Firm—William C. Long

[57] ABSTRACT

A process is provided for the conversion of methane to higher hydrocarbons; methane is first oxidatively coupled to form a product mixture comprised of ethylene, hydrogen, and carbon monoxide, and this product mixture is reacted over a dual catalyst comprised of a metal oxide effective for the reaction of carbon monoxide and hydrogen and a zeolite component effective for the oligomerization of ethylene.

5 Claims, No Drawings

HYDROCARBON PRODUCTION

BACKGROUND OF THE INVENTION

1. Field of the Invention

The present invention relates to an improved process for the production of $C_2+$ hydrocarbons, especially those boiling in the gasoline range, from feed materials containing methane. In particular, the invention provides a process for converting a methane containing feed in an oxidative conversion reaction to a mixture comprised of ethylene, hydrogen, carbon oxides, and unreacted methane, and thereafter converting this mixture to higher hydrocarbons in improved yields by reaction over a dual catalyst which promotes both hydrogen and carbon monoxide reaction and ethylene oligomerization.

2. Description of the Prior Art

Large quantities of natural gas, which is primarily methane, are found at remote sites. Because of transportation difficulties and expense, this natural gas is largely unused.

A great deal of effort and expense has gone into research programs designed to provide improved methods for the conversion of methane (natural gas) to higher boiling hydrocarbons, i.e. $C_2+$ hydrocarbons, which can more readily be transported from remote locations to those locations where the higher hydrocarbons can be used.

In particular, the oxidative conversion of methane to higher hydrocarbons has been the subject of extensive efforts. Both "cofeed" and "redox" mode operations have been studied; cofeed systems being those in which a mixture of methane and gaseous oxidant are contacted at reactive conditions with a solid contact agent, and redox systems being those wherein a solid contact agent comprised of reducible metal oxide is alternately contacted at reaction conditions with methane and with gaseous oxidant. Patents relating to these technologies include the following U.S. Pat. Nos. 4,443,649, 4,444,984, 4,443,648, 4,443,645, 4,443,647, 4,443,644, 4,443,646, 4,449,323, 4,499,324, 4,593,139, 4,489,215, 4,499,322, 4,495,374, 4,544,784, 4,544,785, 4,547,610, 4,547,611, 4,517,398, 4,544,787, 4,547,608, 4,544,786, 4,568,785, 4,629,718, 4,650,781, 4,554,395, 4,560,821, 4,547,607, 4,533,780, 4,523,049, 4,523,050, 4,634,800, 4,608,449, and the like.

In U.S. Pat. No. 4,567,307, above mentioned, there is described a process wherein methane is contacted at reactive conditions with a reducible metal oxide to produce ethylene, and the ethylene is oligomerized to produce higher hydrocarbon products. This patent provides a comprehensive listing of pertinent references showing catalysts, especially shape selective crystalline molecular sieve materials, which are useful to catalyze the ethylene oligomerization.

In PCT International Publication No. WO 86/05176 published Sept. 12, 1986 there is described a process wherein methane in admixture with oxygen is reacted over an oxidative coupling catalyst to produce a product mixture comprised of higher hydrocarbons and this mixture is contacted with an oligomerization catalyst under aromatization conditions to produce a mixture of aromatic hydrocarbon and saturated aliphatic hydrocarbons of higher molecular weight than methane.

Considerable prior art exists which relates to the conversion of synthesis gas, i.e. carbon oxides and hydrogen, to hydrocarbons. See, for example, European publication No. 0,099,715 of British Petroleum, U.S. Pat. No. 4,659,743, *Ind. Eng. Chem. Res.*, 1987, Vol 26, pages 183–188, U.S. Pat. No. 4,487,851, *Journal of Catalysis, Vol.* 107, pages 471-481 (1987), and the like.

Considerable work in the area of conversion of mixtures of ethylene, hydrogen, and carbon monoxide to higher hydrocarbons has been reported by Russian workers. See, for example, the following: *Izvestiya Akademii Nauk SSR, Seriya Khimicheskaya*, No. 4, pp. 772–778, April 1967, *Izvestiya Akademii Nauk SSR, Seriya Khimicheskaya*, No. 5, pp. 1016–1023, May 1967, *Izvestiya Akademii Nauk SSR, Seriya Khimicheskaya*, No. 5, pp. 1059–1065, May 1969, *Izvestiya Akademii Nauk SSR, Seriya Khimicheskaya*, No. 7, pp. 1472–1477, July 1971, *Izvestiya Akademii Nauk SSR, Seriya Khimicheskaya*, No. 7, pp. 1470–1476, July 1967, *Izvestiya Akademii Nauk SSR, Seriya Khimicheskaya*, No. 10, pp. 1812–1817, October 1966, *Izvestiya Akademii Nauk SSR, Seriya Khimicheskaya*, No. 8, pp. 1710–1714, August 1967, *Izvestiya Akademii Nauk SSR, Seriya Khimicheskaya*, No. 6, pp. 1257–1262, June 1967, and *Izvestiya Akademii Nauk SSR, Seriya Khimicheskaya*, No. 12, pp. 2719–2725, December 1971.

Also, in U.S. Pat. No. 4,487,984 there is described the alkylation of an aromatic compound by reacting the aromatic compound with a mixture of carbon monoxide and hydrogen at alkylation conditions with a dual-function catalyst. The catlayst is described as being comprised of (1) a composite of oxides of copper, zinc and aluminum or chromium and (2) an alumino silicate which may be either in crystalline or amorphous form.

SUMMARY OF THE INVENTION

In accordance with the present invention, there is provided a process for the conversion of methane to higher hydrocarbons, especially to hydrocarbons boiling in the gasoline range. In accordance with the invention, a methane containing mixture such as natural gas or a mixture derived from natural gas is first reaced to convert at least a portion of the methane to ethylene by oxidative coupling of the methane containing mixture whereby there is produced a product mixture containing by volume up to 80% unreacted methane, 1% or more hydrogen, 1% or more carbon monoxide and 0% or more ethylene. Subsequently, this ethylene containing mixture is contacted with a dual functioning catalyst comprised of metal oxides such as oxides of Ru, Co, Cu, Zn, Cr, Al and the like, which promote reaction of the carbon oxides and hydrogen together with shape selective zeolites such as ZSM-5 which are known to promote lower olefin oligomerization, under reactive conditions effective to convert both the ethylene and the carbon monoxide and hydrogen to the desired higher hydrocarbon product.

DETAILED DESCRIPTION OF THE INVENTION

The methane fed to the process is conveniently obtained from the abundant sources of natural gas which are available in various parts of the world. Natural gas itself can be used as the starting material, or the natural gas can first be treated to improve its purity and/or methane content. Generally speaking, methane will comprise at least 50%, usually 50-90% of the hydrocarbon mixture which is fed to the oxidative coupling conversion.

Any of the known oxidative synthesis procedures, especially those set forth in the patents cited above, can be employed. It is particularly advantageous to conduct the methane conversion in the cofeed, high velocity mode as this produces a product mixture best suited for conversion over the mixed oxide-zeolite catalyst. By cofeed mode is meant the conversion of a mixture comprised of methane and gaseous oxidant such as molecular oxygen (provided as air, for example) in accordance with procedures set forth in U.S. Pat. Nos. 4,523,049, 4,523,050, 4,634,800, and copending application Ser. No. 07/014,405 filed Feb. 13, 1987, the disclosures of which are incorporated herein by reference.

In general, temperatures in the range of 500° C. to 1200° C. can be employed in the oxidative coupling, preferably 700° C. to 1000° C. Pressures of 0 to 300 psig. are generally suitable. Various added materials such as steam, halogens, and the like, can be incorporated in the feed in accordance with known procedures to enhance the oxidative coupling.

It is especially preferred to conduct the oxidative coupling, as above indicated, in the cofeed mode at high space velocities since mixtures formed at the high space velocity oxidative couplings tend to have a high carbon monoxide content relative to carbon dioxide, i.e., above 1, and are most suitable for subsequent reaction over the dual catalyst.

In general, it is preferred to conduct the oxidative coupling in the cofeed mode at space velocities of at least about 1200 $hr^{-1}$ GHSV and preferably in the range of about 3000 to 12000 $hr^{-1}$ GHSV (based on methane).

As a result of the oxidative coupling of the methane there are produced reaction product mixtures which have the following molar composition:

| Component | Broad Range | Preferred Range |
|---|---|---|
| CO | 1.0–50% | 2–25% |
| $CO_2$ | 0.5–50% | 1–25% |
| $H_2$ | 1.0–50% | 2–20% |
| Steam | 0–50% | 5–40% |
| $C_2=$ | 1.0–50% | 5–25% |
| Methane | 5.0–80% | 10–75% |

In addition, the gas mixtures can also comprise ethane, $C_3$ to $C_7$ hydrocarbons as well as nitrogen and oxygen when derived from cofeed methane conversions.

In accordance with the invention, the product mixture from the oxidative coupling is reacted over a dual catalyst which promotes reaction of CO and hydrogen and which also promotes ethylene oligomerization. The overall result of practise of the invention is a substantial enhancement in the ultimate yield of $C_2+$ hydrocarbons from the methane source.

Reaction temperatures which are employed in the conversion of the ethylene, hydrogen, and carbon monoxide containing mixtures to higher hydrocarbons over the dual functioning catalyst broadly range from 100° to 600° C., preferably 200° to 400° C., while reaction pressures broadly ranging from 0 to 600 psig., preferably 100 to 400 psig., are used.

In accordance with the invention, the mixture comprised of ethylene, carbon oxides and hydrogen is passed at the reaction conditions into contact with the dual functioning catalyst which is comprised of a metal oxide effective for reaction of carbon monoxide and hydrogen and a shape selective zeolite effective for lower olefin oligomerization.

In general, the metal oxide component is comprised of one or more of the oxides of Ru, Co, Cu, Zn, Cr and Al. Co oxides are preferred, followed by Ru, Cu, Zn, Cr and Al oxides in order of declining preference. The shape selective zeolite components of particular interest in the context of the present invention are silaceous, crystalline molecular sieves. Such silica-containing crystalline materials include materials which contain, in addition to silica, significant amounts of alumina. These crystalline materials are frequently named "zeolites", i.e., crystalline aluminosilicates. Silica-containing crystalline materials also include essentially aluminum-free silicates. These crystalline materials are exemplified by crystalline silica polymorphs (e.g., silicalite, disclosed in U.S. Pat. No. 4,061,724 and organosilicates, disclosed in U.S. Pat. No. Re. 29948), chromia silicates (e.g., CAM), ferrosilicates and galliosilicates (see U.S. Pat. No. 4,238,318), and borosilicates (see U.S. Pat. Nos. 4,226,420; 4,269,813; and 4,327,236).

Crystalline aluminosilicate zeolites are best exemplified by ZSM-5 (see U.S. Pat. Nos. 3,702,886 and 3,770,614), ZSM-11 (see U.S. Pat. No. 3,709,979), ZSM-12 (see U.S. Pat. No. 3,832,449), ZSM-21 and ZSM-38 (see U.S. Pat. No. 3,948,758), ZSM-23 (see U.S. Pat. No. 4,076,842), and ZSM-35 (see U.S. Pat. No. 4,016,246). Examples of processes for the conversion of low molecular weight olefins over zeolites are found in U.S. Pat. Nos. 2,972,643; 3,325,465; 3,960,978; 3,972,832; 4,021,502; 4,044,065; 4,150,062; and 4,254,295. Also see U.S. Pat. Nos. 4,417,086 and 4,417,087 wherein oligomerization processes employing fluidized crystalline molecular sieves are disclosed.

The catalyst which is employed can comprise a simple admixture of the metal oxide component with the zeolitic material. Alternatively, the zeolite can be impregnated with a precursor of the metal oxide and calcined to produce a suitable final catalyst. Catalysts produced according to the teaching in U.S. Pat. No. 4,487,984 are among those which are suitable for use in this invention.

The invention is illustrated by the following examples

EXAMPLE 1

A feed gas mixture comprising by volume 30% steam, 35% air and 35% methane is contacted in a 0.5 inch I.D. alumina tubular reactor with a solid 14–30 mesh Li/B/Mn/MgO mixed oxide catalyst having the atomic ratio 0.5 B:0.5 Li:1.0 Mn:2.5 Mg. The catalyst is prepared by mixing appropriate amounts of MgO with boric acid, lithium hydroxide and manganese dioxide, ball milling the resulting slurry, spray drying and calcining the milled slurry, and pelletizing, crushing, and screening the calcined material The feed gas space velocity is 9600 $hr^{-1}$ GHSV (on methane) and temperature in the reactor is 925° C. Pressure is essentially atmospheric. After 5 minutes at equlibrated conditions, methane conversion is 21.9% and selectivity to $C_2+$ hydrocarbons is 56.2%. The reactor effluent contains 3.9% by volume $H_2$. The selectivity to various products is shown in Table 1.

The reactor effluent from the oxidative coupling is pressured to about 315 psig. and passed directly to a second reaction zone wherein the effluent is contacted with a dual catalyst for oligomerization and reaction of CO with $H_2$. The catalyst is a mixture of equal parts by weight of reduced 10 wt. % Co on $SiO_2$, and shape selective ZSM-5 zeolite, all 14–30 mesh. The reaction is carried out at 315° C. in a 0.5 inch I.D. alumina reactor encased in a metal sheath. Feed gas space velocity is 2 h$^{-1}$ WHSV based on ethylene with respect to the zeolite. The products are collected and analyzed Conversion of CO is 15.4%, conversion of hydrogen is 38.0%, and conversion of ethylene is 86.0%. Selectivity to $C_5^+$ hydrocarbons is 61.4% as a result of reaction over the dual catalyst. Overall $C_2^+$ yield based on methane fed is 13.0%.

The following Table 2 shows the composition of the oxidative coupling effluent which is fed to the dual catalyst reactor and the composition of the effluent from the dual catalyst reactor, as well as the $C_1$ mole percent selectivity to various products based on ethylene conversion in the dual catalyst reaction zone.

EXAMPLE 2

This example illustrates an alternative oxidative coupling reaction to produce a reaction mixture to be fed to the second, dual catalyst reaction.

A 3% by weight Li (as LiOH) on $MnO_4$ $SiZn_2$ catalyst in a 14–30 mesh size is placed in a 0.5 inch I.D. alumina tubular reactor. The same feed mixture as in Example 1 is passed over the catalyst at essentially atmospheric pressure and 950° C. Space velocity is 4800 hr$^{-1}$ GHSV on methane. After 30 minutes at equilibrated conditions, methane conversion is 20.9% and selectivity to $C_2^+$ hydrocarbon is 58.8%. Hydrogen content of the effluent is 3.6% by volume, selectivities to CO and $CO_2$ are 26.8% and 14.4%, respectively.

Table 3 shows selectivities to various materials. The reactor effluent is suitably fed directly to a dual catalyst reactor in accordance with the invention.

TABLE 1

| Example | Conditions | % CH4 Conv. | % C2+ Sel. | % Selectivity | | | | | | |
|---|---|---|---|---|---|---|---|---|---|---|
| | | | | C2= | C2 | C3 | ≧C4 | CO | CO2 | coke |
| 1 | 925° C., 9600 GHSV, 6.7 WHSV Feed: 30% steam, 35% air, 35% methane | 21.9 | 56.2 | 37.6 | 9.4 | 5.4 | 3.8 | 10.0 | 23.9 | 0 |

TABLE 2

| Feed Composition Effluent from oxidative coupling of Methane Mole % | | Product Composition Effluent from oligomerization —CO/H2 Utilization Mole % | C1 Mole % Sel. Based on C2= Conv. during oligomerization —CO/H2 Utilization Mole % |
|---|---|---|---|
| H2 | 3.8 | 2.3 | — |
| Steam | 53.6 | 54.7 | — |
| N2 | 27.2 | 27.8 | — |
| CH4 | 7.5 | 7.7 | — |
| C2= | 2.8 | 0.4 | — |
| C2 | 0.7 | 1.2 | 19.7 |
| C3 | 0.4 | 0.5 | 4.8 |
| ≧C4 | 0.3 | 2.2 | 72.6 |
| CO | 1.5 | 1.3 | — |
| CO2 | 1.8 | 1.9 | 2.3 |
| O2 | 0.4 | 0 | |
| C2+ yield | 12.3 | 13.0 | (coke 0.6) |

TABLE 3

| Example | Conditions | % CH4 Conv. | % C2+ Sel. | % Selectivity | | | | | | |
|---|---|---|---|---|---|---|---|---|---|---|
| | | | | C2= | C2 | C3 | ≧C4 | CO | CO2 | coke |
| 3 | 950° C., 4800 GHSV, 3.4 WHSV Feed: 30% steam, 35% air, 35% methane | 20.9 | 58.8 | 41.5 | 10.7 | 4.5 | 2.1 | 26.8 | 14.4 | 0 |

EXAMPLE 3

This example illustrates an alternative oxidative coupling reaction to produce a reaction mixture to be fed to the second, dual catalyst reaction.

A 3% by weight Li (as $LiBO_2$) on $CaTiO_3$ catalyst in a 14–30 mesh size is placed in a 0.5 inch I.D. alumina tubular reactor. The same feed mixture as in Example 1 is passed over the catalyst at essentially atmospheric pressure and 950° C. Space velocity is 4800 hr$^{-1}$ GHSV on methane. After 30 minutes at equilibrated conditions, methane conversion is 14.0% and selectivity to $C_2^+$ hydrocarbons is 51.7. Hydrogen content of the effluent is 2.4% by volume, selectivities to CO and $CO_2$ are 43.6% and 4.7%, respectively.

Table 4 shows selectivities to vaious materials. The reactor effluent is suitably fed directly to a dual catalyst reactor in accordance with the invention.

TABLE 3

| Example | Conditions | % CH4 Conv. | % C2+ Sel. | % Selectivity | | | | | | |
|---|---|---|---|---|---|---|---|---|---|---|
| | | | | C2= | C2 | C3 | ≧C4 | CO | CO2 | coke |
| 3 | 950° C., 4800 GHSV, 2.3 WHSV Feed: | 14.0 | 51.7 | 35.3 | 11.5 | 3.6 | 1.3 | 43.6 | 4.7 | 0 |

TABLE 3-continued

| Example | Conditions | % CH$_4$ Conv. | % C$_2$+ Sel. | % Selectivity | | | | | | |
|---|---|---|---|---|---|---|---|---|---|---|
| | | | | C$_2$= | C$_2$ | C$_3$ | ≧C$_4$ | CO | CO$_2$ | coke |
| | 30% steam, 35% air, 35% methane | | | | | | | | | |

EXAMPLE 4

This example illustrates an alternative conversion of mixtures such as are produced by oxidative coupling of methane as above illustrated by reaction over a dual functioning catalyst which contains a shape selective olefin oligomerization zeolite and a metal oxide which promote sreaction between hydrogen and carbon monoxide.

A physical mixture of 2.5 cc (1 gram) of a reduced 10% Co on SiO$_2$ and 1.8 cc (1 gram) of shape selective ZSM-5 zeolite (all 14–30 mesh) is charged to a ½″ I.D. alumina reactor encased in a metal sheath. To the fixed bed reactor at 315° C. and 315 psig. is fed a mixture comprised by volume of 13% H$_2$, 10% C$_2$=, 2% N$_2$, 62% CH$_4$ and 13% CO at a rate of 290 cc/min (2 hr$^{-1}$ WHSV C$_2$= with respect to the zeolite), representing the effluent mixture from oxidative coupling of methane. The gaseous and liquid products are collected for 6 hours. The cumulative effluent gases are analyzed by gas chromatography (FID and TCD) and the Mole percentages of H$_2$, C$_2$=, N$_2$, CH$_4$, CO, CO$_2$, C$_2$, C$_3$'s, C$_4$'s, C$_5$'s, C$_6$'s, >C$_7$'s and Coke are determined.

Analysis of the products shows 15.4% CO conversion, 38.0% H$_2$ conversion and 86.0% C$_2$= conversion with 61.4% C$_5$+ selectivity. See Table 5.

TABLE 5

| Product | C$_1$ Mole % Selectivity |
|---|---|
| CO$_2$ | 2.3 |
| C$_2$ | 19.7 |
| C$_3$'s | 4.8 |
| C$_4$'s | 11.2 |
| C$_5$'s | 7.6 |
| C$_6$'s | 2.7 |
| >C$_7$'s | 51.1 |
| Coke | 0.6 |

EXAMPLE 5

A comparative example is carried out using as catalyst just the ZSM-5, i.e., no Co on silica is used. The reactor is charged with 1 cc (0.5 grams) of a shape selective zeolite admixed with 1 cc (2 grams) of 14–30 mesh Al$_2$O$_3$. The reaction is carried out at 345° C. for 4 hours. With a feed rate of 145 cc/min a WHSV of 2 hr$^{-1}$ C$_2$= with respect to the zeolite was obtained.

Analysis of the products indicates 0% CO conversion, 8.8% H$_2$ conversion and 95.2% C$_2$= conversion with 52.4% C$_5$+ selectivity. See Table 6.

TABLE 6

| Product | C$_1$ Mole % Selectivity |
|---|---|
| CO$_2$ | 0 |
| C$_2$ | 2.1 |
| C$_3$'s | 15.1 |
| C$_4$'s | 29.7 |
| C$_5$'s | 13.7 |
| C$_6$'s | 5.6 |
| >C$_7$'s | 33.1 |

TABLE 6-continued

| Product | C$_1$ Mole % Selectivity |
|---|---|
| Coke | 0.7 |

EXAMPLE 6

This Example illustrates an alternative conversion of mixture such as are produced by oxidative coupling of methane as above illustrated by reaction of a dual functioning catalyst which contains a shape selective olefin oligomerizing zeolite and a metal oxide which promotes reaction between hydrogen and carbon monoxide.

To a shape selective zeolite ZSM-5 sized to 14–30 mesh is added a solution of Ru$_3$(CO)$_{12}$ to the point of incipient wetness. The impregnated zeolite is dried and reduced to form a catalyst comprised by weight of 5% Ru on the ZSM-5.

The catalyst is tested as described in Example 4 with the following exceptions: the reaction is carried out at 345° C. with a feed of 34% H$_2$, 2% N$_2$, 10% C$_2$=, 13% CO and 41% CH$_4$. The reactor is charged with 2 cc (1 gram) of 5% Ru on ZSM-5 diluted with 2.6 cc (4 grams) of 14–30 mesh alumina.

Analysis of the products show 45.1% CO conversion, 65.1% H$_2$ conversion, and 99.6% C$_2$= conversion with 26.7% C$_5$+ selectivity. See Table 7.

TABLE 7

| Product | C$_1$ Mole % Selectivity |
|---|---|
| CO$_2$ | 6.0 |
| C$_2$ | 45.3 |
| C$_3$'s | 10.3 |
| C$_4$'s | 11.3 |
| C$_5$'s | 5.1 |
| C$_6$'s | 2.3 |
| >C$_7$'s | 19.3 |
| Coke | 0.4 |

EXAMPLE 7

For comparative purposes, a test is carried out in a manner similar to that of Example 6, with the following exceptions: the reactor is charged with 1 cc (0.5 gram) of a shape selective zeolite, ZSM-5 diluted with 2.5 cc (4 grams) of Al$_2$O$_3$, all of 14–30 mesh. The reaction is carried out at 345° C. at a feed rate of 145 cc/min to give a WHSV of 2 hr$^{-1}$ C$_2$=, with respect to the zeolite. The feed consists of 34% H$_2$, 2% N$_2$, 10% C$_2$, 13% CO and 41% CH$_4$.

Analysis of the products indicates 0% CO conversion, 27.9% H$_2$ conversion, and 97.6% C$_2$= conversion with 55.0% C$_5$+ selectivity. See Table 8.

TABLE 8

| Product | C$_1$ Mole % Selectivity |
|---|---|
| CO$_2$ | 2.7 |
| C$_2$ | 2.1 |
| C$_3$'s | 13.9 |
| C$_4$'s | 26.1 |

TABLE 8-continued

| Product | $C_1$ Mole % Selectivity |
|---|---|
| $C_5$'s | 12.3 |
| $C_6$'s | 3.5 |
| >$C_7$'s | 39.2 |
| Coke | 0.2 |

It will be apparent from the above comparisons that the metal oxide catalyst component is essential for conversion of the carbon monoxide. In the runs where zeolite alone was employed, no carbon monoxide conversion is observed.

In order to further illustrate the suprising nature of the invention, a catalyst effective for the hydropolymerization of mixtures of ethylene, carbon monoxide, and hydrogen was prepared as described in *Izvestiya Akademii Nauk SSr, Seriya Khimicheskaya*, No. 12, pp. 2719-2725, December, 1971. Comparison runs were then made with this catalyst, both alone and in admixture with zeolitic oligomerization catalyst. The results achieved are shown in the following examples:

EXAMPLE 9

To a one liter beaker is added 12 g of high purity MgO, containing no detectable sulfur, and a solution of 59.26 g of $Co(NO_3)_2.6H_2O$ dissolved in 250 cc. of distilled water. While vigorously stirring this dispersion there is added 7% solution of $(NH_4)_2CO_3$ (25.55 g of $(NH_4)_2CO_3.H_2O$ dissolved in 340 cc. of distilled water (10% molar excess of $(NH_4)_2CO_3$). The resulting solids, consisting of cobalt carbonate ($CoCO_3$) precipitated onto MgO, are collected on a filter funnel. These are washed with distilled water, dried at 110° C. and reduced with 100% hydrogen at 500° C. for 5 hours.

According to the Russian article, when a mixture of ethylene, carbon monoxide, and hydrogen, the mixture containing 3 mol % carbon monoxide and the ratio of ethylene to hydrogen being 2.5-2.7, is reacted over the above catalyst at 190° C. and atmospheric pressure at a space velocity of 100 $hr^{-1}$, carbon monoxide conversion of 51.1% and yield of hydrocarbons of 42.1% is achieved.

EXAMPLE 10

When the above run is repeated at the more severe conditions of 315° C. and 315 psig with a feed comprised by volume of 13% hydrogen, 13% carbon monoxide, 10% ethylene, 2% nitrogen, 3% carbon dioxide, and 59% methane at 2 $hr^{-1}$ WHSV, there is obtained 7.1% carbon monoxide conversion, 44.9% hydrogen conversion, and 72.3% ethylene conversion with a selectivity to $C_5+$ hydrocarbons of 23.2%.

EXAMPLE 11

When the catalyst prepared as above described is admixed with an equal weight of shape selective zeolite (ZSM-5) and Example 10 is repeated using this mixture, conversion of carbon monoxide increases to 20.7%, hydrogen conversion increases to 59.5%, and ethylene conversion increases to 93.9% with a selectivity to $C_5+$ hydrocarbons of 44.2%.

We claim:

1. The process for the production of higher hydrocarbons from methane which comprises reacting a methane containing feed gas by oxidative coupling to form a first product mixture comprises of 1.0-50 mol % CO, 0.5-50 mol $CO_2$, 1.0-50 mol % $H_2$, 0-50 mol % steam, 1.0-50 mol % $C_2=$, and 5.0-80 mol % methane, reacting said first product mixture in a second reaction over a catalyst comprised of both a metal oxide component effective for the reaction of hydrogen and carbon monoxide, and a shape selective zeolite component effective for the oligomerization of ethylene, and recovering higher hydrocarbons from the product of the second reaction.

2. The process for the production of higher hydrocarbons from methane which comprises reacting a feed gas mixture comprised of methane and gaseous oxidant at oxidative coupling reaction conditions effective to form a first product mixture comprised of 2-25 mol % CO, 1-25 mol % $CO_2$, 2-20 mol % $H_2$, 5-40 mol % steam, 5-25 mol % $C_2=$, and 10-75 mol % methane, reacting said first product mixture in a second reaction over a catalyst comprised of both at least one oxide of Co, Ru, Cu, Zn, Cr and Al and a shape selective zeolite effective for oligomerization of ethylene, and recovering higher hydrocarbons from the product of the second reaction.

3. The method of claim 2 wherein the gaseous oxidant is oxygen.

4. The process of claim 2 wherein the methane and gaseous oxidant are reacted at 500°-1200° C. and at a space velocity of at least 1200 $hr^{-1}$ WHSV based on methane.

5. The process of claim 4 wherein the space velocity is 3000 to 12000 $hr^{-1}$ WHSV based on methane.

* * * * *

UNITED STATES PATENT AND TRADEMARK OFFICE

Certificate

Patent No.: 4,849,571                                                                                                    Patented: July 18, 1989

On petition requesting issuance of a certificate for correction of inventorship pursuant to 35 U.S.C. it has been found that the above-identified patent, through error and without any deceptive intent, improperly sets forth the inventorship. Accordingly, it is hereby certified that the correct inventorship of this patent is:
John A. Sofranko and Anne M. Gaffney.

Signed and Sealed this Twentieth day of February, 1990

WILLIAM R. DIXON

*Supervisory Primary Examiner*
*Patent Examining Group 110*